United States Patent [19]
Manian et al.

[11] Patent Number: 5,221,454
[45] Date of Patent: Jun. 22, 1993

[54] DIFFERENTIAL SEPARATION ASSAY

[75] Inventors: Bala S. Manian, Los Altos Hills; Vartan Ghazarossian, Menlo Park, both of Calif.

[73] Assignee: Biometric Imaging Inc., Mountain View, Calif.

[21] Appl. No.: 904,854

[22] Filed: Jun. 25, 1992

Related U.S. Application Data

[62] Division of Ser. No. 828,407, Jan. 31, 1992, Pat. No. 5,137,609.

[51] Int. Cl.$^5$ .................... G01N 27/26; G01N 27/447
[52] U.S. Cl. ............................. 204/299 R; 204/182.8; 204/180.1; 356/344
[58] Field of Search ............ 204/299 R, 182.8, 182.7, 204/182.9, 180.1; 356/344

[56] References Cited

U.S. PATENT DOCUMENTS 5,055,415 10/1991 Imai et al. .................... 204/182.3
5,096,557 3/1992 Simons ......................... 204/299 R

OTHER PUBLICATIONS

R. G. Nielsen et al., "Separation of antibody-antigen complexes by capillary zone electrophoresis, isoelectric focusing and high-performance size-exclusion chromatography", *Journal of Chromatography*, 539 (1991), pp. 177–185.

*Primary Examiner*—John Niebling
*Assistant Examiner*—John S. Starsiak, Jr.
*Attorney, Agent, or Firm*—Schneck & McHugh

[57] ABSTRACT

An electrophoresis-based assay system for detection of one or more target substances, i.e. an analyte tagged with fluorescent binding agents. The analyte is reacted with an excess amount of fluorescently tagged binding agent. The reaction mixture is subjected to electrophoresis and the migration of bound and free fluorescent substances are timed at a location where there is a spatial and optical differentiation of the two substances. An optical detector supplies signals corresponding to fluorescent amplitudes of the two substances. The free fluorescent substance arrives at a time expected from calibration runs. This optical signal is a marker for a second time, either earlier or later, when the bound substance should have arrived. Recorded data is searched to establish the relation between free and bound dye among the recorded optical signals. An absence of a bound dye signal infers the absence of target analyte in a sample. The amounts of bound and unbound amounts of the same fluorescent substance may be related by ratio of amplitudes of the optical signals so that the amount of target analyte may be estimated.

13 Claims, 3 Drawing Sheets

DIFFERENTIAL SEPARATION ASSAY

This is a divisional of copending application Ser. No. 07/828,407 filed on Jan. 31, 1992 now U.S. Pat. No. 5,137,609.

DESCRIPTION

1. Technical Field

The invention relates to an assay for molecular or microbiological agents and in particular to a fluorescence marker-based electrophoretic system for detecting such agents.

2. Background Art

In U.S. Pat. No. 4,811,218 M. Hunkapiller et al. teach a DNA sequencing system using a multiple lane electrophoresis apparatus. Fluorescent dyes are attached to molecules moving through the lanes. A moving illumination and detection system scans the multiple lanes. Four color data points are recorded for each of several lanes at a particular time at a fixed distance down the gel. Through a complex analytic procedure, the four colors are related to the concentrations of four dye-labeled DNA components. The object is to identify concentrations of A, C, G, or T or G, G+A, C+T or C which are DNA piece endings where A=adenosine, C=cytosine, G=guanine and T=thymine. Peak concentrations of a particular dye label are matched with particular bases in DNA sequences.

In U.S. Pat. No. 4,890,247 Sarrine et al. describe an apparatus which robotically handles a plurality of liquid samples in test tubes, applies the samples to electrophoresis matrices and then carries out electrophoresis. The electrophoretically separated molecules are illuminated with fluorescent light. An analog signal is produced, representing the scanned field of view. A computer stores intensity levels of the analog signal and performs densitometric analysis to read the electrophoretic data. Densitometry is a conventional prior art technique for reading such data.

In an article entitled "Affinity Electrophoresis" by Vaclav Horejsi, reported in "Enzyme Purification and Related Techniques", W. Jakoby ed., Academic Press, 1984, p. 275 a novel type of electrophoresis is described. One lane of the gel medium is impregnated with immobilized ligands capable of reacting with a migrating macromolecule, while another lane, a control gel, is untreated. Thus, a comparison can be made, using electrophoresis, between a macromolecule sample retarded by the affinity gel lane and a similar sample in the control gel lane. In a variation of this technique, the gel may incorporate an antibody which interacts with a migrating antigen. The two lanes may be calibrated so that different degrees of retardation, for different concentrations of the migrating macromolecule, are known. Moreover, microscopic beads treated with ligands can be entrapped in the gel and similarly serve as a retardant. Beads have the advantage of tight packing in the gel if they are of appropriate size. Activation of the gel involves partial cross-linking so that the gels do not melt on heating. Alternative methods of gel preparation are described, all with the result that a macromolecular retardant is immobilized. Electrophoresis proceeds in the usual way.

While the analytical systems of the prior art are very useful for DNA analysis and the like, they are not suited for routine clinical laboratory applications where the target substance is a large molecule or pathogen, such as a single macromolecule or a bacterium. Clinical labs have a need for rapidly analyzing body fluids for an increasingly larger number of target biochemical substances present at low concentrations that are indicators of various diseases such as cardiovascular diseases, immune disorders, cancer, microbial infection, etc. Moreover, the current increase and severity of sexually transmitted diseases places an additional burden on laboratories as more tests are needed. An object of the invention is to devise a rapid, sensitive and precise assay system for biochemical substances and pathogens especially suited to, but not limited to, clinical laboratories.

SUMMARY OF THE INVENTION

The above object has been achieved in an assay system for substances of human origin or derived from pathogens which are typically the subjects of clinical lab assays, hereafter called target analytes. In a procedure, a binding agent with fluorescent properties becomes a fluorophore, which is combined with a known amount of target analyte, with the fluorophore present in an excess amount of known concentration. The binding agent can be an antibody, antigen, lectin, receptor, enzyme substrate or inhibitor or protein ligand or other chemical or biochemical with specific affinity for a corresponding molecule. The binding agent is specific for a particular substance of human or animal origin or substance derived from a pathogen. These substances could be of diagnostic utility for human or animal diseases or infectious diseases or biotherapeutic utility. Besides binding with the target analyte, the excess amount of binding agent which has a relatively different mobility than the target analyte and the analyte-binding agent pair and serves as a reference pointer or marker for the target analyte. Differences in mobility arise because of differences in charge-to-mass ratios.

The sample containing both the bound and free fluorescent binding agents are subjected to electrophoresis in a gel. "Bound" binding agent is that which has reacted or complexed with another substance. "Free" binding agent is that which has not reacted. A slit or pinhole is used to limit illumination of the gel to a narrow track or spot. The free fluorescent binding agent, having a known and different mobility than the bound material will move past the stationary viewing track. This serves as an internal marker indicating that the assay system is functioning properly. The bound fluorescent substance may move past the viewing track prior to or subsequent to the unbound material. By means of prior calibration, a time "window" is associated for motion of one substance past the slit or pinhole relative to the other. Motion of one substance past the slit creates an expectation of the arrival of the other within predetermined limits. With the peak detected signal corresponding to the free substance being used as a reference, in the actual run if the bound material does not arrive within the expected window, any other peak obtained outside the window is considered an artifact. The expected arrival times of free fluorescent substance peaks are determined by calibration runs, as well as by peak levels. The intensities of bound and free fluorescent substances at the track are recorded and the two substances are associated by analysis of the time separation between signal peaks.

As mentioned above, a calibration procedure establishes expected times when free and bound binding agent will pass the track where migration times are measured and recorded. These expected times are used to search for the presence of a target substance where the presence is uncertain. For example, if the calibration run establishes that the unbound binding agent will pass the track at a first time and the bound binding agent will pass the track at a second time, the time difference, averaged over a number of runs, creates expected times of arrival at the track in particular gels. When an unknown substance is mixed with a binding agent specific to the target analyte, in an amount in excess of what will react with the target substance, there will be electrophoretic migration of free and bound binding agent. The binding agent and the target substance, if present, will have the same fluorescent wavelength. As electrophoresis of the mixture is conducted, the times when substances having the fluorescent characteristic reach the slit are measured and recorded. After recording, the data is searched for each peak exhibiting the fluorescent wavelength. The time differential between the arrival of bound and free binding agent at a slit is applied to each peak to see if a second peak lies at the differential time, within certain statistical limits called a "window". If so, the second peak is paired with the first peak to establish a bound and free dye relationship which reflects bound and free binding agent. The presence of bound binding agent in turn indicates the presence of target substance and allows quantitation of target substances as described below.

Since the fluorescently tagged binding agents are specific to target analytes, several different tags of different fluorescent wavelengths may be used in the same sample and gel lane. A filter wheel is used to observe one wavelength at a time at the slit or pinhole. For each color, a time domain association is formed of the amplitude of the free fluorescent substance, and the amplitude of the bound substance as they move past a slit. As a further step, amplitude ratios may be compared to calibration measurements to determine the presence and exact concentration of target analytes. Such amplitude ratios preferably use the area under each peak, rather than the peak height, for the ratio computation. When the term "amplitude" is used in connection with such ratios, the area under the peak is intended. Electrophoretic separation is based on differing charge/mass ratio, charge alone or charge/mass/shape contributions and can be optimized for a given analyte-binding agent combination.

When multiple fluorescent substances are used, the wavelength separation is preferably at least 10 nm. By observing the passage of free and bound dye-macromolecule at a single location within a track, signal interferences due to any non-uniformities in the gel, such as polymerization irregularities, bubbles, etc. are obviated.

The invention rapidly predicts, in real time, the results of electrophoresis, without waiting for completion of migration of the target substance or without waiting for production of colored or fluorescent materials by the separated biochemicals.

BEST MODE FOR CARRYING OUT THE INVENTION

Figure 1:
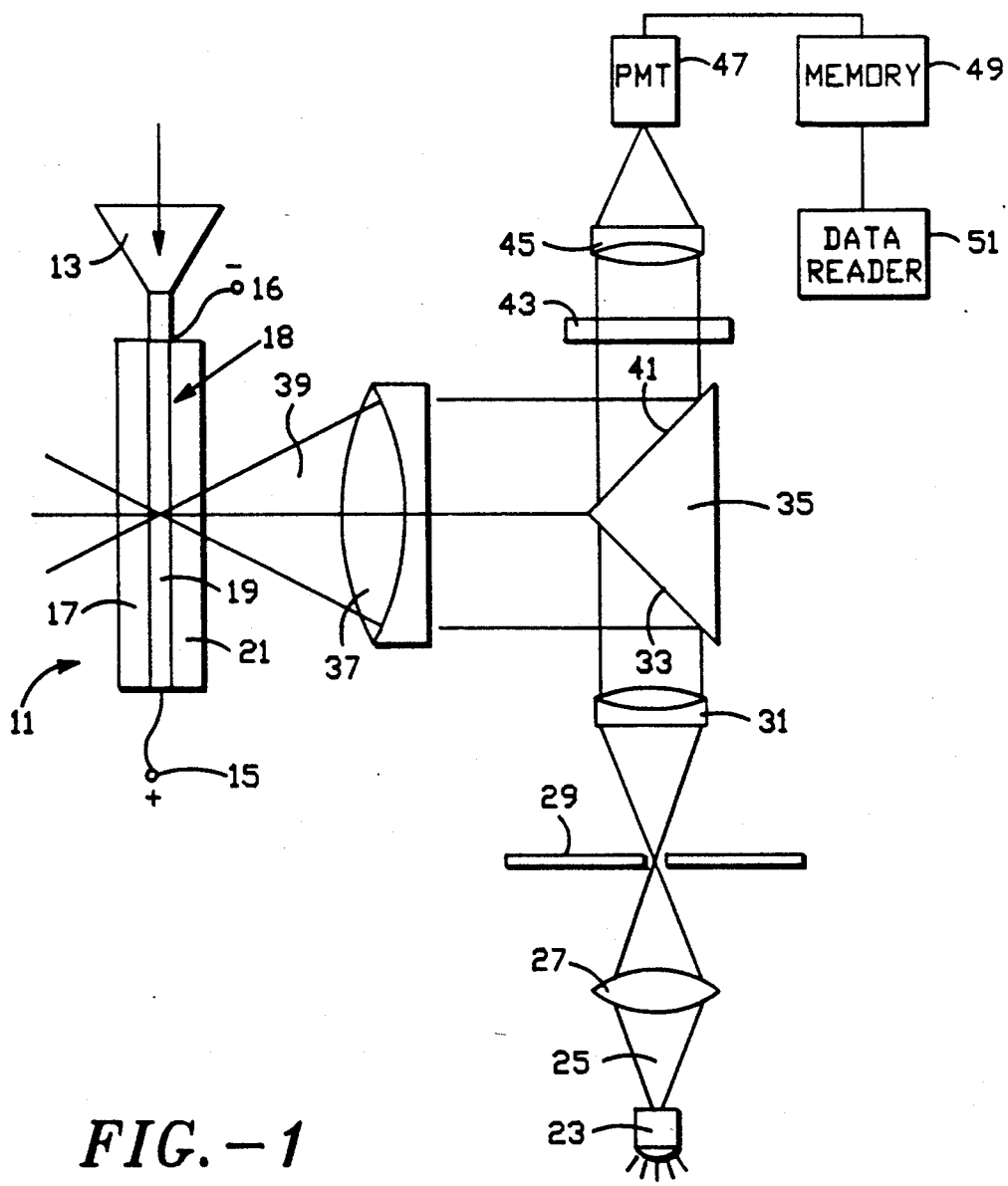
FIG. 1 is a plan view of the apparatus of the present invention.

With reference to FIG. 1 a single lane gel electrophoresis apparatus 11 having a well 13 at one end with a negative voltage terminal 16 and a positive high voltage electrode terminal 15 at an opposite end. The electrophoresis apparatus consists of a conventional single lane 18 having a substrate 17, a gel layer 19 and a protective glass cover 21 The substrate is usually a self-supporting material which may be glass, Mylar (trademark) or any well known gel support. The gel itself is usually polyacrylamide or agarose, although other gel materials such as synthetic acrylamide substitutes may also be used. Uniform polymerization and freedom from bubbles and irregularities are desirable properties. The glass cover is preferably nonreflective glass which merely serves as a protective cover for the gel. The well 13 is normally positioned vertically so that it will receive a sample without spillage. The well funnels a prepared sample toward the gel. The well may combine a stacking and separating gel and creates a spot of sample material on the gel. High voltage is then applied to the gel at terminals 15, 16 and charged ions migrate toward the positively charged voltage electrode. The end of the gel near well 13 is maintained at negative or ground potential so that there is a substantial potential difference from one end of the gel to the distant end.

The sample which is placed in well 13 is a fluid, frequently a fractionated blood sample. Blood may be pre-processed to remove constituents which will interfere with the assay. Removal may be by filtering, absorption, centrifuging or precipitating either the desired or undesired components so that a desired target analyte may be obtained for electrophoresis. The desired target analyte must be one for which there is a specific binding agent. Fluorescent tags such as those commercially available are manufactured by Molecular Probes Inc. of Oregon which specializes in dyes or dyed beads that can be covalently attached to binding agents. Where target analytes are found in larger structures, such as pathogenic agents, then such a dye-binding agent conjugate would be appropriate for tracking that pathogenic agent. Monoclonal antibodies can now be manufactured so that the behavior of this binding agent is uniform and predictable for many assays. Monoclonal antibodies are more expensive than polyclonal antibodies, but the antibodies have greater specificity, are directed toward single epitopes, are easy to produce in large quantities and are generally more useful and cause precise separation of bound and free material.

The tagged binding agent is supplied in excess so that the reaction with the analyte will be driven to completion, or nearly to completion in a reasonable or convenient amount of time. The amount of excess tag should not be more than twenty times the amount of expected maximum level bound tag, although the number may range between 2 and 50, approximately. The tagging substance should alter the mass to charge ratio when combined with the analyte and subjected to an electrophoretic field.

A strongly emitting light source, such as light emitting diode or laser 23 is used to generate a beam 25. The LED 23 has an output power of about 50 mW in a wavelength band which will excite fluorescence in the fluorescent tagging material. Such excitation radiation is known as actinic radiation. The beam is intercepted by a focusing lens 27 which directs the beam through a slit aperture in barrier 29. Light emerging from the slit is divergent and is intercepted by the collimating lens 31. The beam is then directed onto a reflecting surface 33 which is part of a prism 35. The reflective surface 33 is at a 45 degree angle to the beam so that the reflected beam makes a 90 degree angle with the incident beam. The reflected beam is directed toward focusing lens 37 where the beam passes through one half of the focusing lens, while the other half is reserved for light traveling in the opposite direction, reflected from gel layer 19. Light passing through the focusing lens carries an image of the slit 29 which is directed onto the gel layer 19.

Fluorescent light emitted from tagged complex and some reflected light from the gel layer travels in a retro-beam 39 to the left half of focusing lens 37. Note that one half of the focusing lens is used by light travelling in each direction. The right half is used by the incoming beam, while the left half is used by the retrobeam. From there, the retro-beam is directed to reflecting surface 41 which is part of prism 35. The retro-beam is passed through a filter 43 which rejects any light other than the desired wavelength from the fluorescent target. Light transmitted through the filter is directed toward focusing lens 45. From there the beam is directed to a light detector, such as photomultiplier tube 47 with a slit located at the image plane of the gel.

The time of arrival of the fluorescent substances is measured relative to the starting time, i.e. the application of high voltage which initiates electrophoretic migration. Since the arrival time is not precise, but rather is a Gaussian curve, the peak time is recorded. Each target substance and the corresponding fluorescent binding agent are subject to the same procedure in the calibration run. In calibration runs a mean migration time to the measurement slit or pinhole is determined. Then, the standard deviation is determined for the time of arrival of the free binding agent, as well as for the bound target substance. In the present invention, it is necessary to know the mean migration time, i.e., the expected arrival times of bound and free binding agent for specific target substances because the times will be used to search for target analyte in a sample where the target substance is possibly present, but not necessarily present. The difference in arrival times between the bound and free binding agent may be used to establish a time window so that the arrival of one member may be paired with the other member in a search for the other member. If the search reveals that the other member is present within a standard deviation or two, that other material is identified as a member of the pair. If nothing is found within the time window, the first member of the pair is regarded to be an artifact and is discarded.

The output of the photomultiplier tube is maintained in a buffer memory 49 and a ratio may be formed between the signals representing bound and free dye labeled binding agent. A data reader 50 is connected to the buffer memory 49 for receiving recorded signals which represent the fluorescent peaks. The data reader is a computer which correlates the various peaks. Each peak is recorded in order to search for bound and free fluorescent substance in the recorded data. Normally, the time of appearance of the free fluorescent substance could be established from prior calibration times. Once the position of the free fluorescent substance peak is known, a search is conducted for the corresponding bound fluorescent substance which should be located a certain time interval away, within a time window defined by statistical limits. A peak within this window is identified as the bound fluorescent substance, i.e. the target analyte. Next the amplitudes of the identified peaks are examined and a ratio is computed in the data reader 50. The method whereby free fluorescent substance is correlated with bound fluorescent substance is explained further below. The computer also stores calibrations of known concentrations of target substance so that ratios may be compared in order to obtain an estimate of the unknown concentration.

Figure 2:
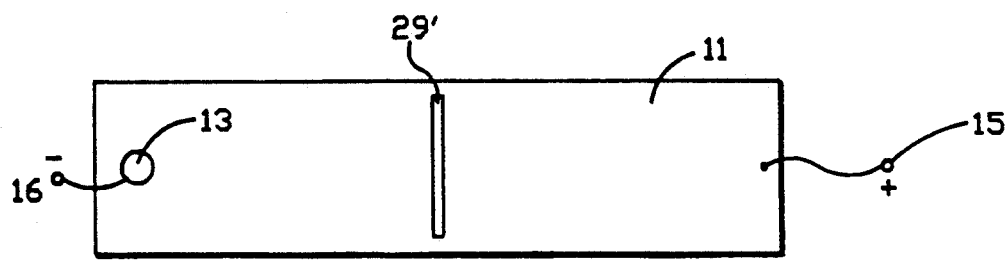
FIG. 2 is a top view of a single gel lane illustrated in FIG. 1.

In FIG. 2, the top view of gel 11 shows that the image 29' of slit 29 falls between a positive high voltage terminal 15 and a spot from well 13, coinciding with negative voltage terminal 16. In operation the high voltage applied to terminal 15 causes migration of bound and free tagged binding agents, which are positively or negatively charged molecules which respond to the electric field from the high voltage supply. The free tagged binding agent will reach the image 29' of slit 29 which is fixed in position at a time different than the bound tagged binding agent. The unbound tagged binding agent serves as one marker for a time window which has the bound tagged binding agent as a corresponding marker, the two markers forming a pair of markers which are separated in time within the statistical limit which is defined.

Figure 3:
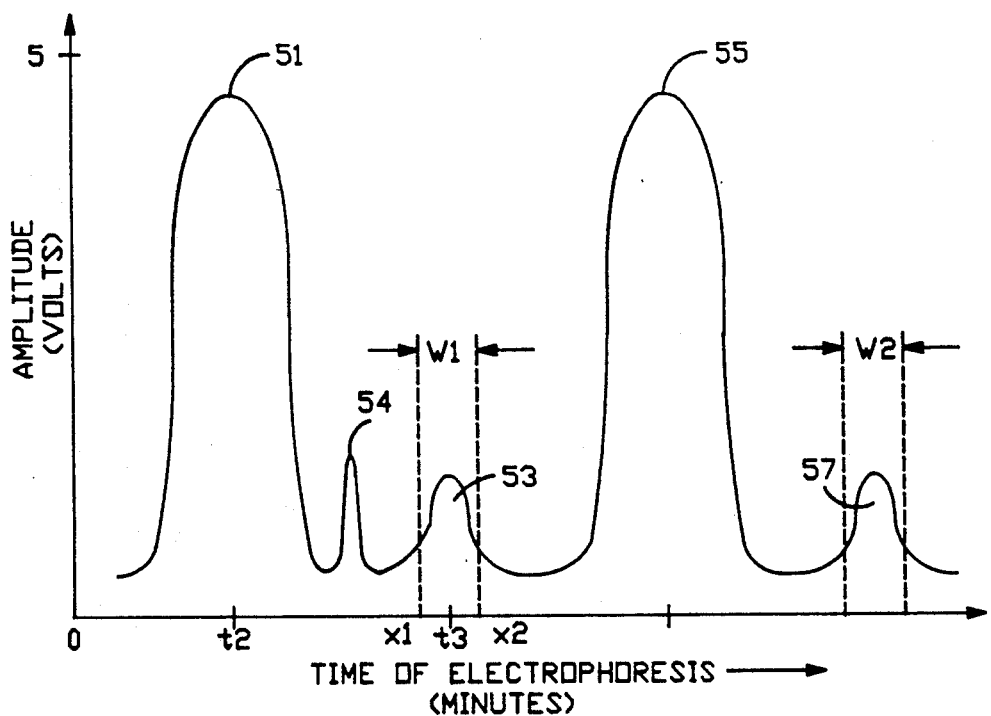
FIG. 3 is a plot of detector signals from unbound and bound fluorescent material.

With reference to FIG. 3, a plot of the detector signal is shown where the horizontal axis is time and the vertical axis is amplitude of the detected signal. As an example, electrophoresis begins at a first time, $t=0$, and the detector is made operative. At a second time, $t_2$, a relatively large peak 51 is observed, representing free fluorescent material of a first color. Another signal 54, discussed below, is detected after peak 51. A time later, $t_3$, a weaker signal 53 of the same color is observed. The peak 53 exists in the midregion of a window, W1, between X1 and X2. The existence of window W1 is established by the strong free fluorescent material signal 51. Peak 53 is within window W1 and is recognized as a bound fluorescent material signal. Peak 54 is not within window W1 and is treated as a false positive or artifact, after being checked to determine whether the signal is not mistaken for the free fluorescent material signal 51. A search of all signals is made to determine the most logical positions for free and bound fluorescent substances. If no signal is found in time window WI, the absence of target analyte is inferred. Each window W acts as a time domain filter, allowing discrimination of spurious fluorescent signals and noise. Note that all signals are recorded and signal discrimination occurs after recording by analyzing recorded data. Even though gel to gel characteristics may vary, the present invention has immunity to most variations because the bound and free fluorescent substances traverse the same path.

The ratio of the two signals represented by the area under the peaks 51 and 53 represents an estimate of the ratio of a bound to free fluorescent substances, after normalizing data relative to calibrations, assuming good binding efficiency. A further time later, another large peak 55 is observed. This represents another free fluorescent binding agent. This defines another time window W2 at a subsequent time and a lesser peak 57 is measured in the window. This is taken to represent a bound fluorescent material. Again, the ratio of bound to free dye is computed and once again the target analyte associated with the second dye may be estimated in concentration.

Figure 4:
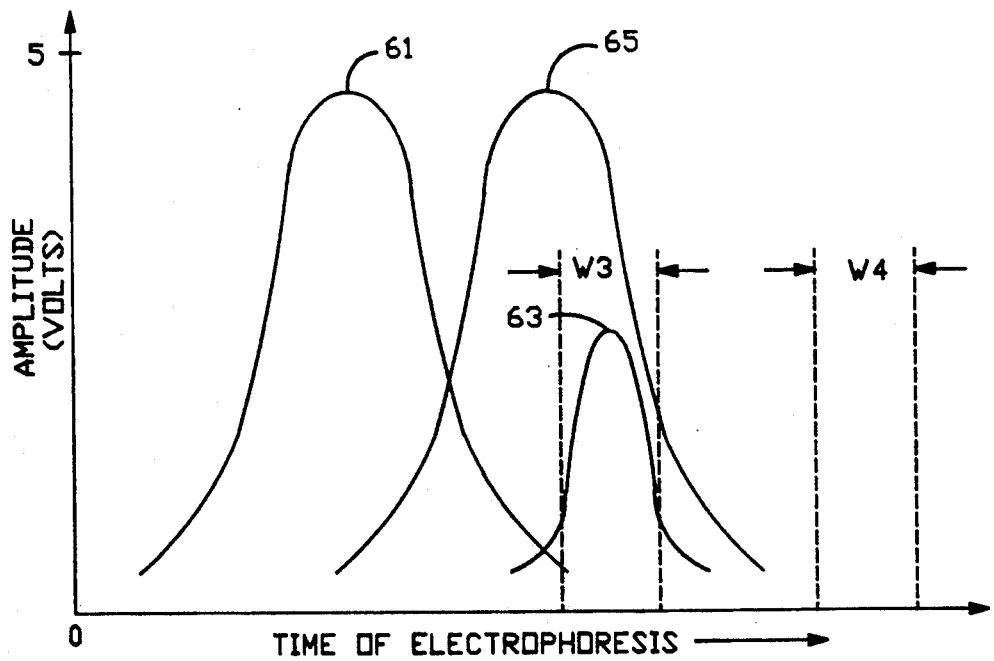
FIG. 4 is a plot of overlapping detector signals of different wavelength from unbound and bound fluorescent material.

It is possible for the peaks to overlap each other as shown in FIG. 4. Here, the first free fluorescent substance peak 61, having a relatively large amplitude, overlaps the second peak 65 of similar amplitude in a test where two different fluorescent substances were used. The second peak 65 is the second free fluorescent substance signal. However, because different colors are used, as separated by the filter 43 in FIG. 1, the two peaks may be separately observed. Peak 61 establishes the time window W3 where a peak 63, representing a bound fluorescently tagged binding agent of a color which is the same as that associated with the unbound peak 61, occurs totally within the second peak 65. Nevertheless, because of the filter 43, peak 63 may be spatially and optically differentiated from peak 65. The ratio of bound to unbound signal amplitudes appears to be about 2:1. The corresponding molecular amounts of bound and unbound tagging material are estimated to be in the same ratio. For the peak 65, a time window W4 is established, but no fluorescent signal is found within the window and so the absence of target analyte is inferred.

Figure 5:
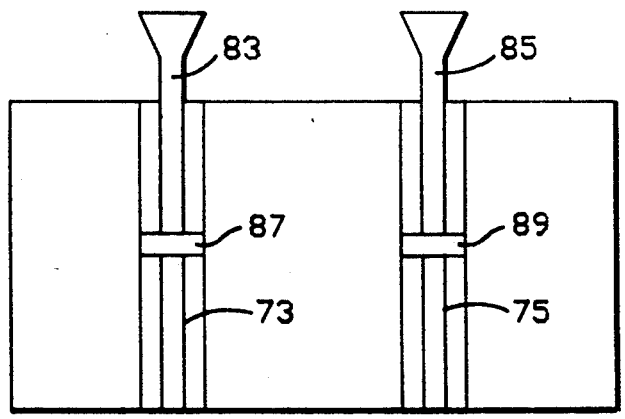
FIG. 5 is a top view of a multiple lane gel arrangement for electrophoresis.

With reference to FIG. 5, a multiple lane electrophoresis sheet gel is shown. The sheet 71 is provided with two lanes 73 and 75. Each of the lanes has a respective well 83 and 85 and a respective slit image 87 and 89. The two lanes are constructed similarly, with the slit image locations in the same position. Lane 73 is used to run a calibrated amount of target analyte and a known amount of free fluorescently labeled binding agent. In lane 75 an unknown amount of target analyte is run with free fluorescently tagged binding agent. The two lanes may be compared to determine the amount of unknown analyte in lane 75. For greater accuracy, multiple runs may be made in lane 73 of various amounts of target analytes so that many ratios may be stored in a memory. A ratio from a run of an unknown amount of target analyte may then be looked up and compared with known ratios, with the best match indicating the amount of target analyte.

One of the advantages of the present invention is that analysis of peaks representing bound and free dye can be computed before electrophoresis is complete, i.e. before the migrating substances reach the distant high voltage electrode. Another advantage is that the present system uses only a single lane of an electrophoresis apparatus so that gel to gel non-uniformities are nulled. It is possible to use a second lane in an electrophoresis device as a reference or calibration, but such calibrations may be done beforehand and results stored in a memory. It is also possible to use a second or third or fourth lane for additional analytes of interest creating panels of relevant analytes. In the prior art, analysis of target analytes usually requires completion of the electrophoresis and subsequent analysis by a plurality of stains, colored or fluorescent substrates, etc. Using the present invention, the analysis may be done in real time as soon as sufficient separation exists between the bound and free fluorescent material. Such a separation can be at a point which is only twenty five percent or thirty three percent of the length of a lane. Once a point is found where adequate separation exists, the image of the slit or pinhole is positioned at that location and then all measurements are made from there. It is also to be noted that this is an open-ended electrophoresis system, i.e. there is no need to stop the electrophoresis at a defined point to get all materials "on scale". Materials that migrate slowly can be detected just as well as fast moving target analytes. Amplitude thresholds may be used as further discrimination against noise and artificial signals.

To discriminate between two or more fluorescently tagged target substances in the same gel lane, different fluorescent wavelengths can be used, so long as filter 43 in FIG. 1 can adequately resolve the different wavelengths. Multiple tests can be run simultaneously, each test associated with a particular wavelength.

EXAMPLE 1

Detection of proteins present in human blood. Creatine kinase is an enzyme present in various mammalian tissue. It occurs in three different forms known as isoenzymes: CK-MM (skeletal), CK-MB (cardiac) and CK-BB (brain). After release from tissue and on circulation in blood the MM and MB forms themselves break down to smaller fragments known as isoforms or subforms. In the event of myocardial infarction, the MB isoenzyme, present in cardiac muscle, is released into plasma. Hence, it serves as a specific diagnostic molecular marker for cardiac ischemia or necrosis. The early and rapid detection of this isoenzyme and its isoforms are very crucial for the diagnosis of myocardial infarction and for initiating thrombolytic therapy.

To perform the test, a blood sample is separated into plasma and red blood cells. The plasma is mixed with excess antibody tagged with a fluorescent dye which is directed against CK-MB. The attachment of fluorescent antibodies for a CK assay is known and is described in U.S. Pat. No. 4,353,982 to M. Gomez et al. If CK-MB is present in plasma, an immune complex consisting of CK-MB and fluorescently tagged antibody will be formed. On application of an electric field, the reaction mixture consisting of the fluorescent immune complex and the unreacted fluorescent antibody, will migrate on the gel. Because of charge and mass differences, the labeled intact immune complex will migrate differently than the labelled antibody. The fluorescence associated with bound and free markers will be detected and arrival times measured and recorded. Free marker is identified by a large peak. Any substance within the expected time of the free substance is regarded to be target analyte. Anything else is an artifact.

Example 2

Detection of the presence of sexually transmitted diseases. Many sexually transmitted pathogens such as chlamydia, herpes, etc. form lesions in the uro-genital area. For detection of these pathogens, samples are taken with a swab directly from the lesion and a number of different types of tests are performed on this extract. These tests include culture and/or immunochemical tests.

After a lesion is sampled with a swab, the swab is treated with a solubilization reagent to liberate microorganisms present. This process will also solubilize target analytes originating from the micro-organisms. This extracted solution will be filtered and reacted with fluorescently tagged antibody so that there is a substantial excess of unreacted tagging substance. The differential assay proceeds as described above.

The methods described above accelerates electrophoresis by varying amounts, depending on where the image 29' of the slit (see FIG. 2) is positioned. If the difference between the charge, mass and shape of the bound and free substances is great, early separation may be expected and the image location 29' may be moved close to well 13. If the difference between the two quantities is not great, the image location 29' needs to be further away from well 13 to allow longer separation time of the bound and unbound fluorescent substance. In either case, the results of electrophoresis are predicted at an earlier time than a complete electrophoresis run.

EXAMPLE 3

Detection of antibody to human serum albumin (HSA). In the following example an antibody against HSA is the target substance which is detected by tagging with fluorescent HSA. HSA, Fraction V, was obtained from Sigma Chemical Company (St. Louis, MO). Monoclonal anti-HSA was obtained from Biospacific Inc., California. Cy5-labelled HSA was synthesized by the coupling of Cy5 fluorescent dye (Biological Research) to HSA and was obtained from Molecular Probes (Eugene, Oregon). This fluorescent substance is the binding agent.

Differential separation assay (DSA) was done as follows: Cy5-labelled HSA (binding agent) was incubated with monoclonal anti-HSA (target) at a final concentration of 400 ng/ml Cy-HSA and 200 ug/ml anti-HSA in 0.09M Tris, 0.08 M borate, 0.26 mM EDTA, pH 8.3. A control sample consisted of Cy5-HSA alone at 400 ng/ml without added antibody. Reactions were performed in 1.5 ml Eppendorf tubes in a total reaction volume of 20 $\mu$l. After incubating the samples at room temperature (20° C.) for 30 minutes, 10 $\mu$l aliquots were loaded onto 6% nondenaturing (8 cm×10 cm×0.75 mm) polyacrylamide gels (Jule labs) containing 0.9 M Tris, 0.8 M Borate, 2.6 mM EDTA, pH 8.3. Electrophoresis was performed at 100V for 40 minutes using a Hoefer Mighty Small SE200 system.

The real time detection of fluorescent proteins during electrophoresis was performed using a He-Ne laser beam focussed at a point 1.3 cm below the wells of the gel. The reflected fluorescence was collected using a photomultiplier (PMT) tube. Data was collected using a Labwindows (Trademark) data acquisition board on an IBMPC and imported into a Microsoft Windows Excel file for analysis and graphics.

Figure 6:
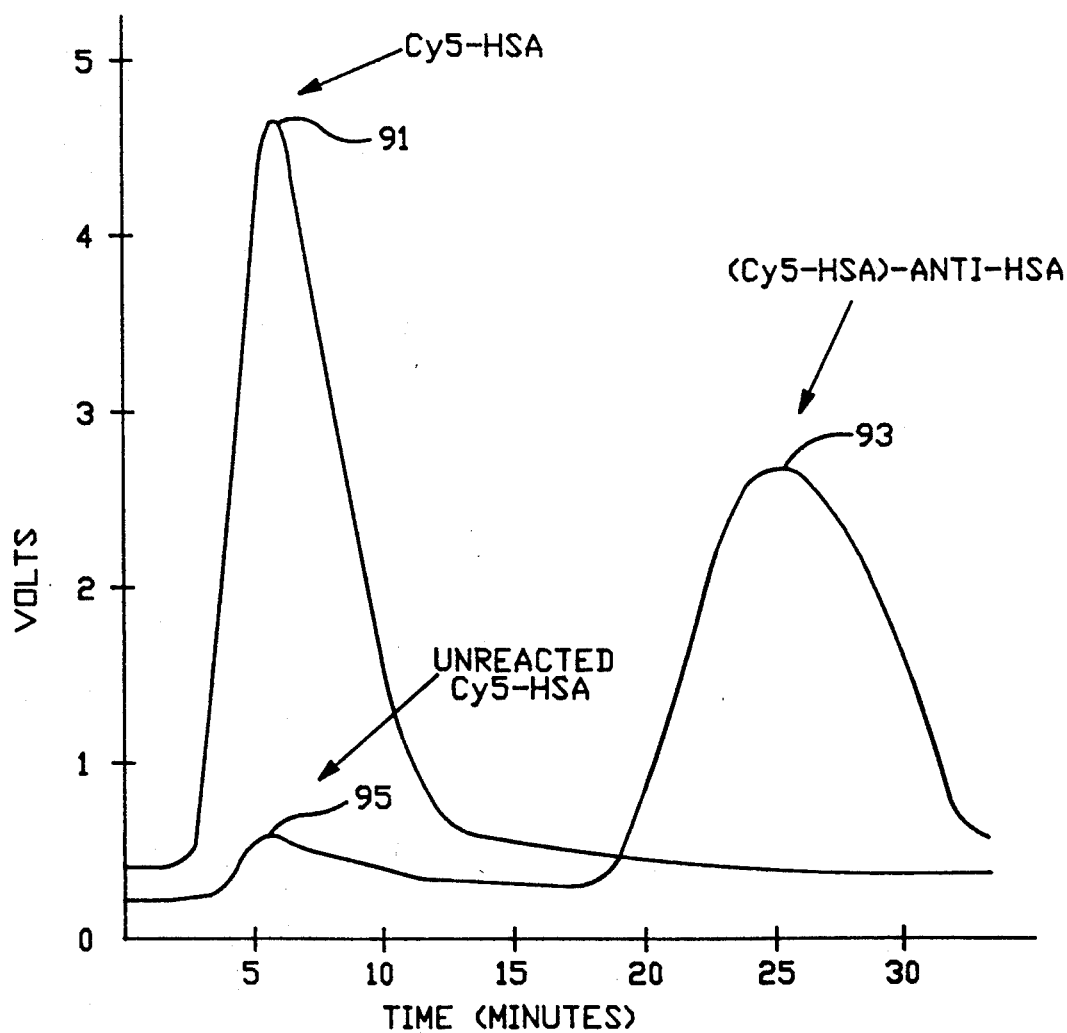
FIG. 6 is a plot of signal amplitude in volts versus time for detection of antibody to human serum albumin.

Samples containing excess Cy5-HSA were reacted with excess monoclonal anti-HSA and then were loaded onto 6% acrylamide gels. FIG. 6 shows signal amplitude as a signal in volts which is proportional to the reflected fluorescence. Separation on this gel system is based on charge/mass characteristics of the proteins and more rapidly migrating species migrate past the laser beam earlier than more slowly migrating protein species.

The Cy5-HSA peak 91 migrates past the laser beam at approximately 8 minutes. This is a calibration run to establish a time for free Cy5-HSA. The immune complex consisting of [{Cy5-HSA}- Anti-HSA], on the other hand, has a peak 93 which migrates past the laser spot at 25.5 minutes. This example demonstrates that the relevant time window for this pair of binding agent (ANTI-HSA) and fluorescent tag (Cy5-HSA) is 17.5 minutes. The 8 minute peak 91 defines the reference position in the data acquisition window for finding the peak 93 of the immune complex ({Cy5-HSA}—Anti-HSA).

We claim:

1. A diagnostic system for determining presence of an analyte comprising,
   an excess amount of fluorescence labeled binding agent forming a complex with a specific target analyte to be determined, the combination having free fluorescence labeled binding agent and bound analyte,
   an elongated migration path for the bound analyte and the labeled binding agent, the bound analyte and the labeled binding agent having different migration rates, said path having a migration start zone and a downstream migration analysis zone,
   means for effecting the migration of the bound analyte and the free labeled binding agent,
   optical means in communication with the analysis zone for timing the migration of fluorescence labeled binding agent and bound analyte from the start zone to the analysis zone, and
   means for comparing the migration times or rates of fluorescence labeled binding agent and bound analyte, whereby the presence of analyte is determined.

2. The system of claim 1 wherein said migration path is an electrophoretic path.

3. The system of claim 1 wherein said binding agent is selected from the group consisting of a fluorescent antibody, antigen, receptor, enzyme substrate, enzyme inhibitor and lectin.

4. The system of claim 1 wherein said complexed target analyte comprises a monoclonal antibody.

5. The system of claim 1 wherein said fluorescent labeled binding agent and bound analyte have substantially different charge-to-mass characteristics.

6. The system of claim 1 wherein said migration path is established in a sheet gel.

7. The system of claim 6 further defined by a plurality of fluorescent labeled binding agents and corresponding bound analytes, wherein said sheet gel contains a plurality of paths, one path having a calibrated amount of bound analyte and a known amount of free fluorescence labeled binding agent.

8. The system of claim 7 wherein said plurality of paths apart from said one path contain the remaining members of said plurality of fluorescent labeled binding agents and corresponding bound analytes.

9. The system of claim 1 wherein said migration path is established in multiple lanes.

10. The system of claim 1 wherein said migration path is established in a single lane.

11. A diagnostic system for detecting target substances during electrophoresis comprising,
    an electrophoresis apparatus having a voltage supply terminal, a gel lane and a sample supply source, the voltage supply terminal establishing a path of migration for electrophoretically mobile substances,
    first optical means including a focused beam, a beam restricting slit or pinhole disposed in the path of the focused beam, and first optical elements projecting an image of the slit or pinhole on the gel lane in said path between the voltage supply terminal and the sample supply source,
    a light detector isolated from light of the beam,
    second optical mans including a reflected beam which is the reflection of the focused beam, a filter and second optical elements projecting a reflected image of the slit onto said detector, said first and second optical elements sharing a focusing lens, a sample of free fluorescent substance and analyte material tagged with fluorescent substance, both being mobile substances in said gel lane, means for measuring and recording times of signals representing detection of fluorescent substances, and a data reader means for correlating the presence of free fluorescent substance with bound fluorescent substance.

12. The apparatus of claim 11 further defined by a prism having first and second reflective surfaces, the first reflective surface inclined at an angle to receive said focused beam and directing said beam to said shared focusing lens and the second reflective surface inclined at an angle to receive the reflected image of the slit and directing said image to the detector.

13. The apparatus of claim 11 wherein a plurality of gel lanes are arranged in parallel relation, one gel lane being a test lane and one or more gel lane being calibration lanes, said slit or pinhole image being in the same relative location in said lanes.

* * * * *